United States Patent
Bestgen et al.

(10) Patent No.: US 12,351,542 B2
(45) Date of Patent: Jul. 8, 2025

(54) SPACERED UREA (METH)ACRYLATES

(71) Applicant: Evonik Operations GmbH, Essen (DE)

(72) Inventors: Sebastian Bestgen, Eschborn (DE); Thorben Schütz, Alsbach-Haehnlein (DE); Silvia Beyer, Ober-Ramstadt (DE); Martin Glock, Darmstadt (DE); William Gordos, Darmstadt (DE)

(73) Assignee: Evonik Operations GmbH, Essen (DE)

(*) Notice: Subject to any disclaimer, the term of this patent is extended or adjusted under 35 U.S.C. 154(b) by 0 days.

(21) Appl. No.: 17/941,017

(22) Filed: Sep. 8, 2022

(65) Prior Publication Data

US 2023/0088931 A1    Mar. 23, 2023

(30) Foreign Application Priority Data

Sep. 10, 2021   (EP) .................... 21195869

(51) Int. Cl.
*C07C 275/12* (2006.01)
*C09D 7/40* (2018.01)
*C09D 7/63* (2018.01)

(52) U.S. Cl.
CPC .............. *C07C 275/12* (2013.01); *C09D 7/63* (2018.01); *C09D 7/68* (2018.01)

(58) Field of Classification Search
None
See application file for complete search history.

(56) References Cited

U.S. PATENT DOCUMENTS

| | | | |
|---|---|---|---|
| 2,847,400 A * | 8/1958 | Bortnick | C08F 20/62 560/222 |
| 4,202,990 A | 5/1980 | Murakami et al. | |
| 4,672,105 A | 6/1987 | Schlosser et al. | |
| 5,395,892 A | 3/1995 | Haeberle et al. | |
| 10,421,872 B1 | 9/2019 | Wendland et al. | |
| 2004/0034190 A1 * | 2/2004 | Janssen | C08F 246/00 526/75 |
| 2014/0228509 A1 | 8/2014 | Yang et al. | |
| 2017/0297355 A1 * | 10/2017 | Kurata | C07C 311/05 |
| 2020/0017725 A1 | 1/2020 | Lee et al. | |
| 2020/0392381 A1 | 12/2020 | Qi et al. | |
| 2022/0024238 A1 * | 1/2022 | Taya | B41M 5/34 |

FOREIGN PATENT DOCUMENTS

| | | |
|---|---|---|
| CN | 109879816 | 6/2019 |
| DE | 2805702 | 8/1978 |
| DE | 3423443 | 1/1986 |
| DE | 4237030 | 5/1994 |
| DE | 10 2012 211908 | 5/2014 |
| EP | 0016518 | 10/1980 |
| EP | 0534666 | 3/1993 |
| EP | 1534688 | 6/2005 |
| EP | 2246403 | 11/2010 |
| EP | 2935485 | 4/2019 |
| EP | 3643729 | 4/2020 |
| JP | WO2012176631 | * 12/2012 |
| WO | 2004/016598 | 2/2004 |
| WO | 2006/086322 | 8/2006 |
| WO | WO 2020175615 | * 9/2020 |

OTHER PUBLICATIONS

English machine translation for Kato et al. WO2012176631 (Year: 2012).*
Extended European Search Report dated Apr. 7, 2022, in European Patent Application No. 21195869.9, 5 pages.
Kröhnke et al., "Antioxidants", Ullmann's Encyclopedia of Industrial Chemistry, pp. 1-36.

* cited by examiner

*Primary Examiner* — Renee Claytor
*Assistant Examiner* — Jennifer C Sawyer
(74) *Attorney, Agent, or Firm* — Grüneberg and Myers PLLC

(57) ABSTRACT

A novel urea (meth)acrylate can be prepared by a process involving reacting a urea containing alcohol or amine with a (meth)acrylate, (meth)acryloyl chloride, (meth)acrylic acid, or (meth)acrylic anhydride. A binder composition includes at least one repeating unit derived from the urea (meth)acrylate. The binder composition can be used in adhesive and coating applications.

12 Claims, No Drawings

SPACERED UREA (METH)ACRYLATES

CROSS-REFERENCE TO RELATED APPLICATIONS

This application claims priority to European Application No. 21195869, filed on Sep. 10, 2021, the content of which is hereby incorporated by reference in its entirety.

BACKGROUND OF THE INVENTION

Field of the Invention

The present invention pertains to novel urea (meth)acrylates, to a binder composition including at least one repeating unit derived from those urea (meth)acrylates, to their preparation and to their use in adhesive and coating applications.

Description of Related Art

Among the vast number of polymerizable functional groups, (meth)acrylate moieties are of particular interest as they can be arbitrarily modified, additionally functionalized, exhibit beneficial safety profiles and are usually liquid or low-melting substances.

Among (meth)acrylates, polymerizable molecules bearing urea moieties are of particular interest, as the polymerizable unit ultimately enables the incorporation of urea moieties into polymeric materials. Thereby, those polymeric materials are equipped with polar, hydrophilic and hydrogen-bonding properties, which may be exploited in adhesive, coating and medicinal/biological applications.

The term "wet adhesion" is used in the paint industry to describe the ability of a paint to retain its adhesive bond to a substrate under wet or high humidity conditions. While oil-based systems are known to retain their adhesive properties under wet or humid conditions, the tendency of many water-based coatings (i.e., latexes) to lose their adhesive properties when wet has limited the usefulness of such coatings. The wet adhesion deficiency of latex paints also makes surfaces painted with such paints less scrub resistant than those surfaces painted with organic solvent-based paints.

Since the use of water-based emulsion polymer systems as protective and decorative coatings for many types of surfaces has become widespread, such systems being used by individuals in homes and in industry, there is a great need for improved wet adhesion thereof. In recent years, the art has recognized the problem of loss of adhesive properties in latex paints and a variety of modifications of such latex systems to improve wet adhesion have been proposed. Chemical incorporation of amine, amide and acetoacetate functionalities into latex polymers has been reported to improve the wet adhesion properties of latex paints. For example, a number of cyclic ureido compounds are known as imparting wet adhesion properties.

One prime and industrially most relevant example is N-(2-methacryloyloxyethyl) ethylene urea (MEEU), in which a cyclic urea moiety is linked to a methacrylate via a C2 unit. Its applications are found in polymerization and/or copolymerization processes in bulk, suspension, emulsion and solution, leading to materials which are used in the plastics, paint, leather, paper and textile industries. For many applications, it is utilized to improve wet adhesion and cohesion properties of emulsion polymers and wet scrub resistance of certain products. In its compounds, it also contributes to corrosion protection.

A slight modification of N-(2-methacryloyloxyethyl) ethylene urea is N-(2-methacrylamidoethyl) ethylene urea (N-MEEU), which simply is a methacrylamide instead of an ester. It is also used as wet adhesion monomer for latex paints and promotes adhesion of polymer resins to metal, glass, concrete and other inorganic substrates in many applications including industrial, maintenance, automotive and architectural. It improves wet adhesion effects and solvent resistance in a wide range of latex systems. It provides high adhesive power, enhanced mechanical properties and improved chemical- and water resistance to the polymer systems.

Although MEEU or N-MEEU have been developed decades ago, both monomers are still up-to-date and play a crucial role in current research activities and inventions. For coatings and adhesives, one may refer to e.g. US2020017725 (A1), EP3643729 (A1), EP2935485 (B1), U.S. Pat. No. 10,421,872 B1, or US2020392381 (A1).

However, both molecules as well as their production processes suffer from major drawbacks. First, the general synthetic procedure of the starting materials 2-hydroxyethyl ethylene urea as well as 2-aminoethyl ethylene urea is hardly modifiable and practically pretty much restricted to a five-membered cyclic urea (imidazolidin-2-one) as well as an amino/hydroxy ethyl substituent at one nitrogen atom of the imidazolidin-2-one moiety. Therefore, the range of urea containing (meth)acrylates is rather restricted to the two above mentioned molecules, known as e.g. VISIOMER® MEEU (Evonik) or SIPOMER® WAM II (Solvay). Second, both products are usually obtained (and commercially distributed) as aqueous solutions or solutions in organic solvents or reactive diluents, which impedes subsequent processes in non-aqueous media (e.g. 3D printing) and applications which do not require solvents or reactive diluents. Third, N-(2-methacrylamidoethyl) ethylene urea is usually made from 2-aminoethyl ethylene urea and an activated methacrylic acid derivative (e.g. methacrylic anhydride, methacryloyl chloride), leading to the formation of often undesired and hardly removable byproducts (e.g. methacrylic acid, hydrochloric acid), which have to be laboriously separated from the product. Consequently, resolving these drawbacks is a worthwhile challenge and synthetic pathways towards anhydrous (water-free) and easily purifiable urea (meth)acrylates are still needed.

In addition, structural derivatives of the known ethylene urea ethyl (meth)acrylates/(meth)acrylamides are particularly desirable, which may ultimately lead to polymeric materials with e.g. improved (wet) adhesion and cohesion, improved anti-corrosion properties, or improved scrub resistance. This could be achieved by chemical tailoring of urea (meth)acrylates, and various synthetic routes are conceivable depending on the targeted modification.

SUMMARY OF THE INVENTION

In accordance with the above, it is an objective of the present invention to provide new (meth)acrylate based monomers for (aqueous) emulsion polymers applied in coatings, which excel in e.g. enhanced adhesion to various substrates, substantial protection from corrosion, erosion and chalking, stain resistance, heat resistance and water resistance (particularly hot water resistance and boiling resistance). It is another objective of the present invention to provide new (meth)acrylate monomers for polymers applied in adhesives, which improve corrosion protection, resistance to staining and which show desirable adhesiveness for various types of materials.

As a result, the inventors have unexpectedly found that various and less polar alternative molecules to MEEU are accessible and one possible, but hardly followed alternative for the synthesis of urea functionalized (meth)acrylates or -amides lies in the synthesis of urea bearing (long-chain) alcohols or amines followed by subsequent (meth)acrylation via direct esterification, transesterification, ester aminolysis or condensation of the amine and (meth)acrylic acid.

Such molecules, i.e. monomer compounds, may be described by the general formula (I):

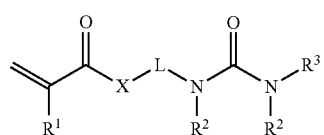

(I)

wherein $R^1$ is —H or -Me;

$R^2$ is H, or a $C_1$-$C_{20}$ linear, branched or cyclic alkyl or aryl group;

$R^3$ is —H, or a $C_1$-$C_{20}$ linear, branched or cyclic alkyl or aryl group, as well as benzene-sulfonyl, tosyl, p-chlorophenyl, adamantyl, 2,6-dimethyl phenyl, 3,5-dimethyl phenyl, and 2,6-dipropyl phenyl;

$R^2$ and $R^3$ may be the same or different, with the exception that if $R^2$=—H, then $R^3$≠—H, and if $R^2$=-Me, then $R^3$≠-Me;

X is —O— or —NH—; and

L is a $C_4$-$C_{20}$ linear, branched or cyclic alkyl or aryl group, in which optionally, one or more carbon atom within the carbon chain is replaced by one or more —O—, —NH— or —S— heteroatoms.

In addition to those specific compounds, the present invention is directed to a composition comprising the compound of formula (I) and at least one polymerization inhibitor.

Further, the present invention provides a process for preparing a monomer compound according to the description below, wherein a urea containing alcohol or amine of the general formula (II)

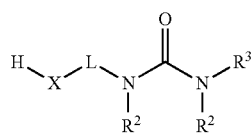

(II)

with X, $R^2$, $R^3$, L as defined above is reacted with a (meth)acrylate species, said (meth)acrylate species being selected from the group consisting of alkyl (meth)acrylates of the general formula (III)

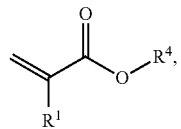

(III)

with $R^4$ being methyl, ethyl, propyl or butyl;

or with (meth)acryloyl chloride, (meth)acrylic acid or (meth)acrylic anhydride.

The present invention also pertains to a binder composition comprising at least one polymer including at least one repeating unit derived from a compound as described above. Said binder composition can be used as a coating or adhesive material, preferably in paints, varnishes, impregnating compositions, adhesives and/or primers.

The Invention Also Includes the Following Embodiments:

1. A compound of the general formula (I):

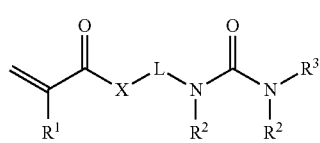

(I)

wherein $R^1$ is —H or -Me;

$R^2$ is H, or a $C_1$-$C_{20}$ linear, branched or cyclic alkyl or aryl group;

$R^3$ is —H, or a $C_1$-$C_{20}$ linear, branched or cyclic alkyl or aryl group, as well as benzene-sulfonyl, tosyl, p-chlorophenyl, adamantyl, 2,6-dimethyl phenyl, 3,5-dimethyl phenyl, and 2,6-dipropyl phenyl;

$R^2$ and $R^3$ may be the same or different, with the exception that if $R^2$=—H, then $R^3$≠—H, and if $R^2$=-Me, then $R^3$≠-Me;

X is —O— or —NH—; and

L is a $C_4$-$C_{20}$ linear, branched or cyclic alkyl or aryl group, in which optionally, one or more carbon atom within the carbon chain is replaced by one or more —O—, —NH— or —S— heteroatoms.

2. The compound according to embodiment 1, wherein $R^2$ and/or $R^3$ is/are selected from hydrogen, methyl, ethyl, propyl, isopropyl, butyl, ethyl hexyl, cyclohexyl and phenyl.

3. The compound according to any one of the preceding embodiments, wherein $R^2$ is hydrogen.

4. The compound according to any one of the preceding embodiments, wherein $R^1$ is -Me, $R^2$ is —H, X is —O—, $R^3$ is selected from methyl, ethyl, propyl, isopropyl, butyl, ethyl hexyl, cyclohexyl and phenyl, and L is butyl, pentyl, hexyl, heptyl, octyl, ethoxyethyl, aminoethyl.

5. The compound according to any one of the preceding embodiments, wherein L is selected from butyl, pentyl, hexyl, heptyl, octyl and ethoxyethyl.

6. A composition comprising the compound of formula (I) and at least one polymerization inhibitor.

7. A process for preparing a monomer compound according to any one of embodiments 1 to 5, wherein a urea containing alcohol or amine of the general formula (II)

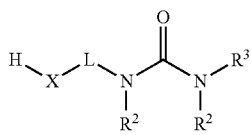
(II)

with X, $R^2$, $R^3$, L as defined above
is reacted with a (meth)acrylate species,
said (meth)acrylate species being selected from the group consisting of alkyl (meth)acrylates of the general formula (III)

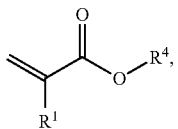
(III)

with $R^4$ being methyl, ethyl, propyl or butyl;
or with (meth)acryloyl chloride, (meth)acrylic acid or (meth)acrylic anhydride.

8. A binder composition comprising at least one polymer including at least one repeating unit derived from a compound according to any one of embodiments 1 to 5.

9. The binder composition according to embodiment 8, wherein the polymer is made of a monomer mixture comprising between 025 wt. % and 20 wt. % of the compound according to any one of claims 1 to 5.

10. The binder composition according to any one of embodiments 8 or 9, wherein the polymer further comprises repeating units of or derived from (meth)acrylic acid, (meth)acrylate, styrene, styrene derivatives and/or vinyl esters.

11. The binder composition according to any one of embodiments 8 to 10, wherein the at least one polymer is an emulsion polymer.

12. The binder composition according to embodiment 11, wherein the emulsion polymer is a core-shell polymer.

13. The binder composition according to any one of embodiments 11 to 12, wherein the particle radius of the emulsion polymers is in the range from 10 to 500 nm.

14. The binder composition according to any one of embodiments 8 to 13, further comprising one or more adjuvants selected from the group consisting of flow improvers, pigments, dyes, thickeners, rheology modifiers, defoamers, surfactants, stabilizers, preservatives, fungicides, algicides, flash rust inhibitors, coalescence agents, dispersing agents, corrosion inhibitors, and/or adhesion promoters.

15. Use of a binder composition according to any one of embodiments 8 to 14 as coating or adhesive material, preferably in paints, varnishes, impregnating compositions, adhesives and/or primers.

DETAILED DESCRIPTION OF THE INVENTION

As indicated above, the inventors have found that (aqueous) emulsion polymers applied in coatings can be improved by replacing currently used urea (meth)acrylates such as MEEU by the new and less polar monomers of the general formula (I). Thereby, adhesion to various substrates can be enhanced and substantial protection from corrosion can be achieved.

In accordance therewith, the present invention relates to polymerizable monomer compounds of the general formula (I):

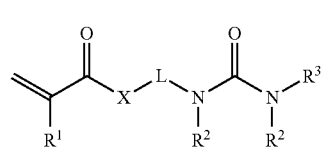
(I)

wherein
$R^1$ is —H or -Me;
$R^2$ is H, or a $C_1$-$C_{20}$ linear, branched or cyclic alkyl or aryl group;
$R^3$ is —H, or a $C_1$-$C_{20}$ linear, branched or cyclic alkyl or aryl group, as well as benzene-sulfonyl, tosyl, p-chlorophenyl, adamantyl, 2,6-dimethyl phenyl, 3,5-dimethyl phenyl, and 2,6-dipropyl phenyl;
$R^2$ and $R^3$ may be the same or different, with the exception that
if $R^2$=—H, then $R^2 \neq$—H, and
if $R^2$=-Me, then $R^3 \neq$-Me;
X is —O— or —NH—; and
L is a $C_4$-$C_{20}$ linear, branched or cyclic alkyl or aryl group, in which optionally, one or more carbon atom within the carbon chain is replaced by one or more —O—, —NH— or —S— heteroatoms.

In the context of the present invention, the term (meth)acrylates includes acrylates (i.e. esters of acrylic acid) and methacrylates (i.e. esters of methacrylic acid), as well as mixtures of methacrylic acid and acrylic acid, and mixtures of acrylates and methacrylates The term "aryl" as used herein includes substituted aryl groups, and in particular alkyl aryl groups, such as Ph-$CH_2$—$CH_2$—. An example for linear alkyl groups in which a carbon atom in the carbon chain is replaced by an O heteroatom is —$CH_2CH_2$—O—$CH_2CH_2$—; an example for linear alkyl groups in which a carbon atom in the carbon chain is replaced by a N heteroatom is —$CH_2CH_2$—NH—$CH_2CH_2$—.

Particularly suitable are urea mono(meth)acrylates (in contrast to crosslinking di-, tri- or tetra(meth)acrylates), in which the functional unit is distant from the polymerizable unit, thereby lowering the monomers' polarity and ultimately enabling different material properties in dispersions and latexes.

$R^2$ may be selected from hydrogen, methyl, ethyl, propyl, isopropyl, butyl, ethyl hexyl, cyclohexyl and phenyl. Preferably, $R^2$ is hydrogen.

$R^3$ may be selected from hydrogen, methyl, ethyl, propyl, isopropyl, butyl, ethyl hexyl, cyclohexyl and phenyl. Preferably, $R^3$ is ethyl, propyl, butyl, phenyl or cyclohexyl.

In one embodiment of the present invention, $R^2$ is hydrogen and $R^3$ is selected from cyclohexyl, phenyl, butyl and ethyl.

In one embodiment of the present invention, $R^1$ is -Me, $R^2$ is —H, X is —O—, and $R^3$ is selected from methyl, ethyl, propyl, isopropyl, butyl, ethyl hexyl, cyclohexyl and phenyl, and L is butyl, pentyl, hexyl, heptyl, octyl, ethoxyethyl, aminoethyl. Advantageously, $R^1$ is -Me, $R^2$ is —H, X is —O—, $R^3$ is selected from phenyl, cyclohexyl, and butyl; and L is selected from butyl, hexyl and ethoxyethyl.

L may be selected from butyl, pentyl, hexyl, heptyl, octyl and ethoxyethyl and is preferably butyl, hexyl, or ethoxyethyl.

Suitable acyclic alkyl urea (meth)acrylates, in which the functional unit is distant from the polymerizable unit ($\geq C_4$) with linkers L=$C_4$-$C_8$; $R^1$=H, Me; $R^2$=H, are e.g.:

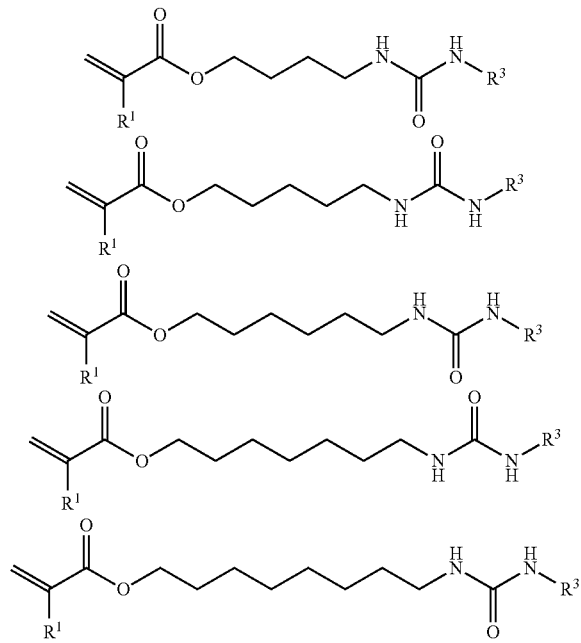

Suitable acyclic alkyl urea (meth)acrylates, in which the functional unit is distant from the polymerizable unit ($\geq C_4$), and in which e.g. one carbon atom is substituted with heteroatoms, such as O, NH, with linkers L=$C_5$ ($C_4$+ heteroatom); $R^1$=H, Me; $R^2$=H are e.g.:

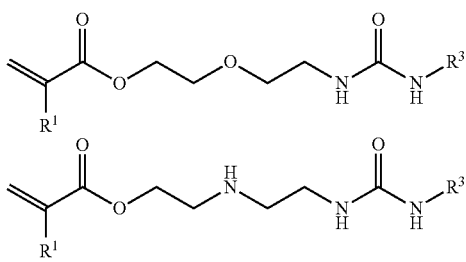

In the above formulae, the $R^3$ residue stems from the respective monoisocyanate starting material applied in the synthesis. Details on the synthesis are described below.

Suitable acyclic alkyl and aryl urea (meth)acrylates, in which the functional unit is distant from the polymerizable unit ($\geq C_4$), with linkers L=$C_4$ and $C_6$; $R^1$=H, Me; $R^2$=H are e.g.:

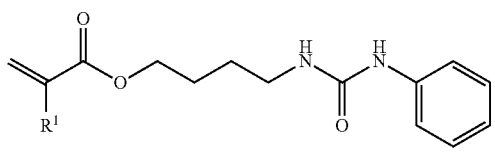

-continued

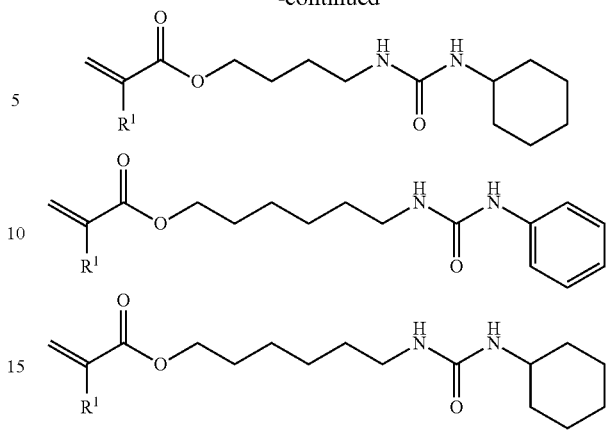

In addition to the compounds disclosed above, the present invention also provides a composition comprising the compound of formula (I) and at least one polymerization inhibitor.

Within the context of the present invention, the terms "(polymerization) inhibitor" and "stabilizer" are used synonymously.

Said at least one polymerization inhibitor may be selected from the group consisting of hydroquinones, hydroquinone ethers such as hydroquinone monomethyl ether or di-tert-butylcatechol, phenothiazine, N,N'-(diphenyl)-p-phenylenediamine, 4-hydroxy-2,2,6,6-tetramethylpiperidin-1-oxyl, p-phenylenediamine, methylene blue or sterically hindered phenols, which are well known in the art. For further details, it is referred to the usual specialist literature, in particular on Kröhnke, C., Schacker, O. and Zäh, M. (2015). Antioxidants. In Ullmann's Encyclopedia of Industrial Chemistry, (Ed.). Preferably, the polymerization inhibitor is selected from hydroquinone monomethyl ether, 2,4-4dimethyl-6-tert-butylphenol, 2,6-di-tert-butyl-4-methylphenol, octadecyl-3-(3,5-di-tert-butyl-4-hydroxyphenyl)-propionate (such as IRGANOX 1076) and 4-hydroxy-2,2,6,6-tetramethylpiperidin-1-oxyl, and mixtures thereof.

For the synthesis of polymerizable monomer compounds of the general formula (I), urea bearing (long-chain) alcohols or amines may be used as starting material. Subsequently, said starting material may be (meth)acrylated via direct esterification or transesterification or ester aminolysis or condensation of an amine and (meth)acrylic acid.

Accordingly, the present invention also pertains to a process for preparing a monomer compound of general formula (I), wherein a urea containing alcohol or amine of the general formula (II)

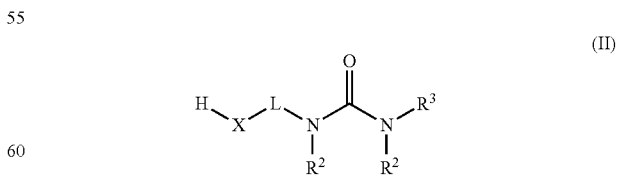

with X, $R^2$, $R^3$, L as defined above
is reacted with a (meth)acrylate species,
said (meth)acrylate species being selected from the group consisting of alkyl (meth)acrylates of the general formula (III)

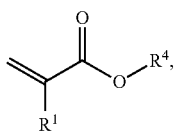
(III)

with R⁴ being methyl, ethyl, propyl or butyl;
or with (meth)acryloyl chloride, (meth)acrylic acid or (meth)acrylic anhydride.

Advantageously, the alkyl (meth)acrylate of the general formula (III) is methyl methacrylate ($R^1$=Me and $R^4$=Me).

The urea containing alcohols and amines can be obtained e.g. by the reaction of aminoalcohols or diamines, and isocyanates, such as $C_1$-$C_{30}$ monoisocyanate compounds such as benzene-sulfonyl isocyanate, tosyl isocyanate, methyl isocyanate, ethyl isocyanate, propyl isocyanate, i-propyl isocyanate, phenyl isocyanate, p-chlorophenyl isocyanate, butyl isocyanate, hexyl isocyanate, t-butyl isocyanate, cyclohexyl isocyanate, octyl iso-cyanate, 2-ethyl hexyl isocyanate, dodecyl isocyanate, adamantyl isocyanate, 2,6-dimethyl phenyl isocyanate, 3,5-dimethyl phenyl isocyanate, and 2,6-dipropyl phenyl isocyanate.

The process as described above makes the utilization of functionalized (meth)acrylate precursors, such as isocyanatoethyl (meth)acrylate, unnecessary.

Further, the thus-obtained process products of formula (I) can be used directly, i.e. without costly and qualitatively burdensome removal steps—for example as a solution in the acryl or methacryl ester—for use as comonomers, particularly in the production of dispersion polymerizates. With the above process, compounds of formula (I) can also be produced as neat liquids or solids according to the present process, for example by being evaporated from solution or by crystallization from the solvent.

Reaction of Starting Material (II) with Alkyl (Meth)Acrylate of the General Formula (III) (Transesterification)

According to the above equation, equimolar amounts of the reaction partners (II) and (III) react to form the desired end products. In practice, however, it has proven to be practical to always keep the starting esters (III) in excess during the reaction. They are used in amounts of 1 to 50, preferably 2 to 10, particularly 3 to 20 moles per mole of (II).

The transesterification as set out above is preferably carried out in the presence of at least one catalyst.

Examples of suitable catalysts are zirconium acetylacetonate and further 1,3-diketonates of zirconium, or calcium. These catalysts are disclosed in e.g. DE 28 05 702 A1.

Further examples for suitable transesterification catalysts are mixtures of alkali metal cyanates or alkali metal thiocyanates with alkali metal halides (such as LiCl); zinc compounds; alkaline earth metal oxides or alkaline earth metal hydroxides (such as CaO, Ca(OH)$_2$, MgO, Mg(OH)$_2$ or mixtures of the above compounds); alkali metal hydroxides; mixtures of alkali metal alkoxides with lithium chloride and/or lithium hydroxide; dialkyltin oxides (such as dioctyl tin oxide (DOTO)), dibutyltin dilaurate, alkali metal carbonates; alkali metal carbonates together with quaternary ammonium salts (such as tetrabutylammonium hydroxide or hexadecyltrimethylammonium bromide); mixed catalysts of diorganyltin oxide and organyltin halide; acidic ion exchangers; phosphomolybdenum heteropolyacids; titanium alcoholates such as titanium isopropoxide; chelate compounds of the metals titanium, zirconium, iron or zinc with 1,3-di-carbonyl compounds; lead compounds (such as lead oxides, lead hydroxides, lead alkoxides, lead carbonates or lead salts of carboxylic acids), amides of a metal of the first main group (such as lithium amide); or mixtures of the above-mentioned catalysts.

In addition, acids or bases can be used to catalyze the transesterification, with exemplary reaction conditions set out in the publications DE 34 23 443 and EP-A-0 534 666.

Particularly preferred catalysts for the transesterification process according to the present invention are tetraalkyl titanates such as titanium isopropoxide as well as alkaline earth metal oxides and hydroxides, such as calcium oxide and calcium hydroxide, which can be combined with alkaline metal salts such as lithium hydroxide or lithium chloride.

The reaction can take place under standard pressure, greater pressure, or in a partial vacuum. It can take place discontinuously or continuously. The starting substances are heated to boiling together and the alcohol $R^4OH$ which is split off is continuously distilled off with the ester, in the form of its azeotrope. Depending on the reaction temperature, the catalyst, and the catalyst amount, the reaction times range from approximately 2 to 15 hours. It is also possible to carry out the reaction in the presence of an inert solvent, for example toluene or cyclohexane, but this is normally not necessary.

After completion of the reaction, excess monomer ester (III) can be removed completely or partially, by distilling it off. The dispersed catalyst is usually removed by filtration, and it is advantageous to do so before distilling off the monomer ester (III), which is mostly present in excess. However, it can also be removed only after partial or complete removal of excess monomer ester (III). The catalyst, when it is recovered in the filtered form, can then be used in other alcoholysis batches, if necessary after being dried.

The reaction of acryl esters and/or methacryl esters with the alcohols or amines of formula (II) (alcoholysis, ester aminolysis) is carried out at temperatures between 30 and 180 degrees C., particularly between 50 and 130 degrees C.

The at least one catalyst may be used in amounts of 0.01 to 5 wt. % used on employed alkyl (meth)acrylate.

Reaction of Starting Material (II) with Activated (Meth) Acrylic Acid Derivatives The activated (meth)acrylic acid derivate used in the present invention can be (meth)acryloyl chloride or (meth)acrylic acid anhydride.

The activated (meth)acrylic acid derivate used in the reaction may be present in an amount of between 0.9 eq. and 2.0 eq, preferably between 1.0 eq. and 1.8 eq. and most preferably between 1.2 eq. and 1.6 eq., based on the amount of the alcohol or amine of the general formula (II).

The reaction of the alcohol or amine of the general formula (II) with the activated (meth)acrylic acid derivate may be carried out under solvent-free conditions, preferably in the presence of at least one catalyst and/or at least one stabilizer (polymerization inhibitor). When (meth)acryloyl chloride is used, bases such as triethylamine can be added, typically in stoichiometric amounts.

The catalyst for reactions with activated (meth)acrylic acid derivatives may advantageously be selected from the group consisting of alkaline metal salts (such as hydroxides, halides, triflates, perchlorates), alkaline earth metal salts (such as hydroxides, halides, triflates, perchlorates), zinc salts (such as hydroxides, halides, triflates, perchlorates), rare earth metal salts (such as halides, triflates, perchlorates), lithium alkoxides, sulfuric acid, triflic acid, lithium or sodium methacrylate, amino-substituted pyridines such as 4-(dimethylamino)-pyridine, or mixtures thereof.

The aforementioned metal salts may be used in anhydrous or in hydrated form. Preferred amounts of catalyst are 0.1 to 10 mol %, particularly 1-5 mol % (relative to alcohol) for lithium alkoxide, sodium hydroxide or magnesium chloride; 0.1 to 2 wt %, particularly 0.5 wt % for sodium methacrylate; 0.1 to 1 wt % sulfuric acid (relative to total reaction mass), particularly 0.3 to 0.4 wt %.

Preferred lithium alkoxide catalysts are LiOMe, LiOEt, LiOiPr, LiOBu and LiOiBu. Sulfuric acid may be used in concentrated or diluted from. Preferably, it is applied in amounts of between 0.01 wt % and 1.0 wt %, relative to the reaction mass. Ion exchange resins, such as amberlyst, can also be used for catalysis.

Preferred catalysts for the process according to the present invention are lithium methoxide, lithium hydroxide, or magnesium chloride, or sodium hydroxide, or sodium (meth) acrylate or sulfuric acid, or mixtures thereof.

Preferably, the activated (meth)acrylic acid derivative is used as its commercially available stabilized species (e.g. VISIOMER® MAAH), stabilized with an inhibitor outlined above.

Preferably, the activated (meth)acrylic acid derivative is used as its commercially available stabilized species (e.g. VISIOMER® MAAH) with either 2000 ppm+−200 ppm 2,4-Dimethyl-6-tert-butylphenol or 1000 ppm+−200 ppm 2,4-Dimethyl-6-tert-butylphenol, thus already introducing one stabilizer into the reaction mixture and also in the final product.

The reaction of the alcohol or amine of the general formula (II) with the activated (meth)acrylic acid derivate may be carried out at a temperature between 0° C. and 130° C., preferably at a temperature between 80° C. and 100° C. and most preferably between 85° C. and 65° C. Usually, reaction takes 3 h to 5 h up to full conversion, but may also be between 1 hour and 24 hours.

The crude reaction mixture may be contacted with methanol prior to subsequent workup of the (meth)acrylate of the general formula (I). In case this intermediate step is conducted, the methanol is preferably added at a temperature between 60° C. and 80° C. The amount of methanol added can be calculated and is 1 to 5 equivalents relative to residual (meth)acrylic anhydride present in the reaction mixture at the end of reaction.

Reaction of Starting Material (II) with (Meth)Acrylic Acid (Esterification)

According to the present invention, the urea-containing alcohol or amine of the general formula (II) can be reacted with (meth)acrylic acid to form the corresponding ester.

This embodiment is particularly preferred for the production of smaller amounts of (meth)acrylic acid esters. According to this embodiment, no low-boiling alcohol is obtained in the reaction, which has to be processed. This configuration therefore leads to cost advantages that can be achieved in particular in smaller systems. Together with the advantages of simpler handling set out above, synergistic effects can be achieved through the use of (meth)acrylic acid as starting material.

Particularly preferred esterifications in which (meth) acrylic acid is reacted with one or more alcohols or amines are preferably catalyzed with acids, in particular sulfuric acid or triflic acid.

The amount of catalyst used can be within a wide range.

In a particularly expedient variant of the esterification according to the invention, all components, such as, for example, the alcohol or amine (II), the (meth)acrylic acid and the catalyst, are mixed, after which this reaction mixture is heated to boiling. When (meth)acrylic acid is reacted with an alcohol or amine, the released water is preferably separated off from the reaction mixture.

The reaction times depend, among other things, on the parameters selected, such as pressure and temperature, for example. However, they are generally in the range from 1 to 24 hours, preferably from 3 to 20 hours and very particularly preferably from 4 to 16 hours. In the case of continuous processes, the residence times are generally in the range from 0.5 to 24 hours, preferably from 1 to 12 hours and very particularly preferably from 2 to 4 hours.

Preferred esterifications take place at a pH of less than 7, preferably less than 5. To determine the pH, part of the reaction mixture can be added to an excess of water (for example 10 times the amount by weight). The pH of the aqueous phase is then determined at 25° C. in a conventional manner.

Inhibitor Concept

To prevent undesirable polymerization of the (meth) acrylates, polymerization inhibitors (stabilizers) can be used in the processes according to the present invention. Suitable inhibitors are described above.

Preferably, the amount of stabilizer at the beginning of the reaction is adjusted to between 0 and 5000 ppm, preferably between 100 ppm and 3000 ppm based on the amount of theoretically expected product at full conversion.

Preferably, the polymerization inhibitor is selected from hydroquinone monomethyl ether, 2,4-Dimethyl-6-tert-butylphenol, 2,6-di-tert-butyl-4-methyl-phenol, Octadecyl-3-(3,5-di-tert-butyl-4-hydroxyphenyl)-propionate (such as IRGANOX 1076) and 4-hydroxy-2,2,6,6-tetramethylpiperidin-1-oxyl, and mixtures thereof. These inhibitors co-precipitate with or remain in the product (meth)acrylates of the general formula (I), meaning that spontaneous polymerizations in the final product can be avoided.

Additional inhibitor may be added, preferably with an amount of additionally added stabilizer at the beginning of the reaction adjusted to between 0 and 1000 ppm based on the amount of theoretically expected product at full conversion, and most preferably with an amount of additionally added stabilizer at the beginning of the reaction adjusted to between 100 and 1000 ppm based on the amount of theoretically expected product at full conversion.

Additional Process Parameters

The reaction can preferably take place with stirring, the stirring speed being particularly preferably in the range from 50 to 2000 rpm, very particularly preferably in the range from 100 to 500 rpm.

The reaction can be carried out either continuously or in batches. A continuous transesterification or esterification can preferably be carried out in plants with several reactors, whereby inter alia the reaction temperature changes and alcohol or water which is released from the low-boiling (meth)acrylic acid ester or which is released from the (meth)acrylic acid can be separated from the reaction system.

Of particular interest are semi-batch processes in which part of the reaction mixture is initially charged. In further steps or continuously, after the start of the reaction, low-boiling esters of (meth) acrylic acid or (meth)acrylic acid can be added to the reaction mixture.

The reaction is preferably carried out under an atmosphere which contains oxygen at most 20% by weight, preferably at most 10% by weight, particularly preferably at most 3% by weight. In this way, complex security measures can be avoided during the implementation, so that many cost advantages are achieved.

The monomers of the present invention may be used more particularly for preparing or for modifying polymers, that may be applied, for example, in binder compositions. The polymerization may take place by any known way.

Such ways include more particularly free-radical, cationic or anionic addition polymerization, it also being possible to employ variants of these addition polymerization processes, such as, for example, ATRP (atom transfer radical polymerization), NMP processes (nitroxide mediated polymerization) or RAFT (reversible addition fragmentation chain transfer).

In accordance therewith, the present invention provides a binder composition comprising at least one polymer including at least one repeating unit derived from a compound according to any one of the monomer compounds of the general formula (I) as described above.

As already described, the monomers of the invention may be reacted by free-radical addition polymerization. Accordingly, the term "unit" arises from the reaction of a double bond, with two covalent bends being constructed. Customarily these units are also referred to as repeating units, if there are two or more of these units in a polymer.

The polymer comprised in the hinder composition is advantageously made of a monomer mixture comprising between 0.25 wt. % and 20 wt. %, preferably 0.5-10 wt. %, and very preferably 1-5 wt. % of the compound according to any one of the monomer compounds of the general formula (I) as described above. Said polymer may further comprise repeating units of or derived from (meth)acrylic acid, (meth)acrylates, styrene, styrene derivatives and/or vinyl esters. The term (meth)acrylates includes linear or branched or cyclic alkyl (meth)acrylates (including those with one or more C atoms substituted with heteroatoms such as N, O, S) aryl (meth)acrylates.

The polymer is preferably made up of at least 80% by weight of methacrylate and acrylate monomers, very particularly preferably exclusively methacrylate and acrylate monomers, based on the total weight of the monomer mixture.

Examples of monofunctional methacrylate and acrylate monomers are, in an incomplete list, methyl(meth)acrylate, ethyl(meth)acrylate, propyl(meth)acrylate, isopropyl(meth)acrylate, n-butyl(meth)acrylate, isobutyl(meth)acrylate, tert-butyl(meth)acrylate, hexyl(meth)acrylate, ethylhexyl(meth)acrylate, isodecyl(meth)acrylate, lauryl methacrylate, cyclohexyl(meth)acrylate, tetrahydrofurfuryl(meth)acrylate, isobornyl(meth)acrylate, benzyl(meth)acrylate, phenyl(meth)acrylate, phenylethyl(meth)acrylate, 3,3,5-trimethyl-cyclohexyl(meth)acrylate. Methods of determining the solubility of organic compounds in water are well known to those skilled in the art.

Said polymer may further comprise repeating units of suitable crosslinking-functional comonomers for use in combination with the novel monomers (I) in self-crosslinking resins. These crosslinking-functional comonomers bear functional carbonyl side groups, precisely keto-groups (ketones, aldehydes), which can react with crosslinking-inducing reagents, such as amines, hydrazines or oxime-blocked isocyanates. Typically, amines, diamines, triamines, hydroxylamines, oximes, oxime ethers, oxyamines, dihydrazines, dihydrazides, trihydrazides or polyhydrazides are used here, for example. Other suitable crosslinkers are described, for example, in WO 2006/086322. Diacetoneacrylamide (DAAM) or acetoacetoxyethyl methacrylate (AAEMA) are most commonly used as crosslinking-functional comonomers. Also, such comonomers are described in eg EP2246403 or DE4237030 or DE102012211908A1.

Styrene derivatives are, for example, α-methylstyrene, chlorostyrene or p-methylstyrene. Examples of vinyl esters are vinyl acetate and relatively long-chain derivatives such as vinyl versatate.

(Meth)acrylic acid is advantageously used in amounts of below 5 wt. %, preferably in amount of below 3 wt. %, based on the total amount of polymer, for stabilizing the polymer dispersion.

The aforementioned monomer mixtures may be reacted, for example, by solution polymerizations, bulk polymerizations or emulsion polymerizations, preferably by means of a free-radical emulsion polymerization.

Methods of emulsion polymerization are set out in references including Ullmann's Encyclopedia of Industrial Chemistry, Fifth Edition. For such a polymerization, an aqueous phase is prepared which as well as water may comprise customary additives, more particularly emulsifiers and protective colloids for stabilizing the emulsion.

This aqueous phase is subsequently admixed with monomers, and polymerization takes place in the aqueous phase. When preparing the polymer dispersion, the monomer mixture may be added batchwise or continuously over a time interval.

In accordance with the above, the at least one polymer applied in the binder composition may be an emulsion polymer, preferably a core-shell polymer.

The emulsion polymerization may be implemented for example as a miniemulsion polymerization or as a microemulsion polymerization. A miniemulsion polymerization is usually characterized by the use of costabilizers or swelling agents, and often long-chain alkanes or alkanols are used. The droplet size in the case of miniemulsions is situated preferably in the ramie from 0.05 to 20 μm. The droplet size in the case of microemulsions is situated preferably in the range below 1 μm, allowing particles to be obtained with a size below 50 nm. In the case of microemulsions use is often made of additional surfactants, examples being hexanol or similar compounds.

The dispersing of the monomer-containing phase in the aqueous phase can take place using known agents. These include, more particularly, mechanical methods and also the application of ultrasound.

When preparing core-shell polymers, it is possible to change the composition of the monomer mixture in steps, with polymerization preferably taking place, before the composition is changed, to a conversion of at least 80% by weight, more preferably at least 95% by weight, based in each case on the total weight of the monomer mixture used.

The progress of the polymerization reaction in each step can be monitored in a known way, as for example by gravimetry or gas chromatography. The monomer composition for preparing the core comprises preferably 50% to 100% by weight of (meth)acrylates, particular preference being given to the use of a mixture of acrylates and methacrylates.

The emulsion polymerization is carried out preferably at a temperature in the range from 0 to 120° C., more preferably in the range from 30 to 100° C. In this context, polymerization temperatures in the range from greater than 60 to less than 90° C., advantageously in the range from greater than 70 to less than 85° C., and preferably in the range from greater than 75 to less than 85° C. have been found to be especially favorable.

The polymerization is initiated with the initiators that are customary for emulsion polymerization. Suitable organic initiators are, for example, hydroperoxides, such as tert-butyl hydroperoxide or cumene hydroperoxide. Suitable inorganic initiators are hydrogen peroxide and also the alkali metal salts and the ammonium salts of peroxodisulphuric acid, more particularly ammonium, sodium and potassium peroxodisulphate. Suitable redox initiator systems are, for example, combinations of tertiary amines with peroxides or sodium disulphite, and alkali metal salts and the ammonium salts of peroxodisulphuric acid, more particularly sodium and potassium peroxodisulphate. In the context of the present invention it is particularly preferred to use organic and/or inorganic initiators.

The stated initiators may be used both individually and in a mixture. They are preferably used in an amount of 0.05% to 3.0% by weight, based on the total weight of the monomer mixture of the respective stage. It is also possible with preference to carry out the polymerization with a mixture of different polymerization initiators having different half-lives, in order to keep the flow of free radicals constant over the course of the polymerization and also at different polymerization temperatures.

Stabilization of the batch is accomplished preferably by means of emulsifiers and/or protective colloids. The emulsion is preferably stabilized by emulsifiers, in order to obtain a stable low viscous dispersion. The total amount of emulsifier is preferably 0.1% to 15%, more particularly 0.2% to 10% and with particular preference 0.5% to 5% by weight, based on the total weight of the monomer mixture used.

Particularly suitable emulsifiers are anionic or nonionic emulsifiers or mixtures thereof, more particularly alkyl sulphates, preferably those having 8 to 18 carbon atoms in the alkyl radical, alkyl and alkylaryl ether sulphates having 8 to 18 carbon atoms in the alkyl radical and 1 to 50 ethylene oxide units; sulphonates, preferably alkylsulphonates having 8 to 18 carbon atoms in the alkyl radical, alkylarylsulphonates having 8 to 18 carbon atoms in the alkyl radical, esters and monoesters of sulphosuccinic acid with monohydric alcohols or alkylphenols having 4 to 15 carbon atoms in the alkyl radical; where appropriate these alcohols or alkylphenols may also have been ethoxylated with 1 to 40 ethylene oxide units; phosphoric acid partial esters and their alkali metal and ammonium salts, preferably alkyl and alkylaryl phosphates having 8 to 20 carbon atoms in the alkyl or alkylaryl radical and 1 to 5 ethylene oxide units; alkyl polyglycol ethers, preferably having 8 to 20 carbon atoms in the alkyl radical and 8 to 40 ethylene oxide units; alkylaryl polyglycol ethers, preferably having 8 to 20 carbon atoms in the alkyl or alkylaryl radical and 8 to 40 ethylene oxide units; ethylene oxide/propylene oxide copolymers, preferably block copolymers, favourably having 8 to 40 ethylene oxide and/or propylene oxide units.

The particularly preferred anionic emulsifiers include, more particularly, fatty alcohol ether sulphates, diisooctyl sulphosuccinate, lauryl sulphate, C15-paraffinsulphonate, it being possible to use these compounds generally in the form of the alkali metal salt, more particularly the sodium salt. These compounds may be obtained commercially, more particularly, under the commercial designations Disponil® FES 32, Aerosol® OT 75, Texapon® K1296 and Statexan® K1.

Judicious nonionic emulsifiers include tert-octylphenol ethoxylate with 30 ethylene oxide units and fatty alcohol polyethylene glycol ethers which have preferably 8 to 20 carbon atoms in the alkyl radical and 8 to 40 ethylene oxide units. These emulsifiers are available commercially under the commercial designations Triton® X 305, Tergitol® 15-S-7, Marlipal® 1618/25 and Marlipal® O 13/400.

With preference it is possible to use mixtures of anionic emulsifier and nonionic emulsifier. The weight ratio of anionic emulsifier to nonionic emulsifier can judiciously be in the range from 20:1 to 1:20, preferably 2:1 to 1:10 and more preferably 1:1 to 1:5. Mixtures which have proved to be especially appropriate are those comprising a sulphate, more particularly a fatty alcohol ether sulphate, a lauryl sulphate, or a sulphonate, more particularly a diisooctyl sulphosuccinate or a paraffin sulphonate, as anionic emulsifier, and an alkylphenol ethoxylate or a fatty alcohol polyethylene glycol ether having in each case preferably 8 to 20 carbon atoms in the alkyl radical and 8 to 40 ethylene oxide units, as nonionic emulsifier.

Where appropriate the emulsifiers can also be used in a mixture with protective colloids. Suitable protective colloids include partially hydrolysed polyvinyl acetates, polyvinylpyrrolidones, carboxymethyl, methyl, hydroxyethyl and hydroxypropyl cellulose, starches, proteins, poly(meth)acrylic acid, poly(meth)acrylamide, polyvinyl sulphonic acids, melamine-formaldehyde sulphonates, naphthalene-formaldehyde sulphonates, styrene-maleic acid and vinyl ether-maleic acid copolymers. If protective colloids are used they are used preferably in an amount of 0.01% to 1.0% by weight, based on the total amount of the monomers. The protective colloids may be included in the initial charge before the start of the polymerization, or metered in. The initiator may be included in the initial charge or metered in. It is also possible, furthermore, to include a portion of the initiator in the initial charge and to meter in the remainder.

The polymerization is preferably started by heating the batch to the polymerization temperature and initial-charge introduction and/or metering of the initiator, preferably in aqueous solution. In this case it is possible for a portion of the monomers to be included in the initial charge to the reactor and for the remainder to be metered in over a defined time period. In general it is advantageous to polymerize the portion of the monomers that has been included in the initial charge to the reactor, and only then to commence the feed. Alternatively, to the initial-charge introduction of a defined quantity of monomer, the feed may be interrupted for a number of minutes after, for example, 1%-5% of the monomers have been metered in. The metered feeds of emulsifier and monomers may be carried out separately or, preferably, as a mixture, more particularly as an emulsion in water.

The emulsion polymerization may be carried out within a broad pH range. The pH is preferably between 2 and 9. In one particular embodiment the polymerization is carried out at pH levels between 4 and 8, more particularly between 6 and 8. It is also possible for the dispersion to be adjusted, after the polymerization, to a pH range which is preferred for the application. For pigmented coating systems the range is generally 8-9 or above.

If crosslinking-functional comonomers are used in combination with the novel monomers (I) in self-crosslinking resins, crosslinking can be performed using commonly applied crosslinking reagents and procedures well known in the art, i.e. via addition of diamines and/or dihydrazides (such as ADH and as mentioned above) and/or blocked crosslinking reagents such as blocked hydrazides, which are described in e.g. US 2014/0228509, EP0016518, DE4237030 or EP2246403.

In order to accelerate a desired self-crosslinking, the dispersion can be admixed with catalysts for the catalysis of self-crosslinking, in which case this ought to take place preferably shortly before the application of the coating materials. These catalysts include, among others, alkali metal carbonates, alkali metal cyanides, sodium acetate, dilute aqueous alkalis and dilute hydrochloric acid.

To improve the durability of the polymer dispersion and especially for the purpose of preventing premature self-crosslinking, the pH may be set at around the neutral point, i.e., in the range from 6 to 9, preferably ≥7.

The molecular weight of the polymers is within wide limits initially uncritical. While particularly hard and solvent-resistant coating materials having good mechanical properties are desired, then a very high molecular weight may be useful. The reaction parameters for obtaining a high molecular weight are known. Thus, in that case it is possible in particular to omit the use of molecular weight regulators.

Coating materials which have particularly good and easy processing qualities may also contain polymers having a relatively low molecular weight, the solvent resistance and the hardness of these coatings attaining a relatively high level. Preferably these polymers with particularly good processing properties may have a molecular weight below 1,000,000 g/mol, preferably below 500,000 g/mol and more preferably below 250,000 g/mol. The molecular weight may be determined by means of gel permeation chromatography (GPC) against a PMMA standard.

Polymers, more particularly emulsion polymers, having a low molecular weight can be obtained by the addition of molecular weight regulators to the reaction mixture before or during the polymerization. For this purpose it is possible to use sulphur-free molecular weight regulators and/or sulphur-containing molecular weight regulators, which are well known in the art.

The sulphur-free molecular weight regulators, include, for example, dimeric α-methylstyrene (2,4-diphenyl-4-methyl-1-pentene), enol ethers of aliphatic and/or cycloaliphatic aldehydes, terpenes, β-terpinene, terpinolene, 1,4-cyclohexadiene, 1,4-dihydro-naphthalene, 1,4,5,8-tetrahydronaphthalene, 2,5-dihydrofuran, 2,5-dimethylfuran and/or 3,6-dihydro-2H-pyran; dimeric α-methylstyrene is preferred.

As sulphur-containing molecular weight regulators it is possible with preference to use mercapto compounds dialkyl sulphides, dialkyl disulphides and/or diaryl sulphides. The following polymerization regulators are cited by way of example: di-n-butyl sulphide, di-n-octyl sulphide, diphenyl sulphide, thiodiglycol, ethylthioethanol, diisopropyl disulphide, di-n-butyl disulphide, di-n-hexyl disulphide, diacetyl disulphide, diethanol sulphide, di-tert-butyl trisulphide and dimethyl sulphoxide. Compounds used with preference as molecular weight regulators are mercapto compounds, dialkyl sulphides, dialkyl disulphides and/or diaryl sulphides. Examples of these compounds are ethyl thioglycolate, 2-ethylhexyl thioglycolate, cysteine, 2-mercaptoethanol, 1,3-mercaptopropanol, 3-mercapto-propane-1,2-diol, 1,4-mercaptobutanol, mercaptoacetic acid, 3-mercaptopropionic acid, mercaptosuccinic acid, thioglycerol, thioacetic acid, thiourea and alkyl mercaptans such as n-butyl mercaptan, n-hexyl mercaptan or n-dodecyl mercaptan. Polymerization regulators used with particular preference are mercapto alcohols and mercaptocarboxylic acids.

The molecular weight regulators are used preferably in amounts of 0.05% to 10%, more preferably 01% to 5% by weight, based on the monomer mixture used in the polymerization. In the polymerization it is of course also possible to employ mixtures of polymerization regulators. Furthermore, polymerizations using the molecular weight regulators to reduce the minimum film formation temperature (MFFT) of the polymers obtainable thereby may be employed. In accordance with this preferred embodiment, the fraction of molecular weight regulators may be calculated such that the polymers, or the coating materials of the invention, have a minimum film formation temperature (MFFT) of not more than 60° C., more preferably not more than 50° C. and very preferably not more than 40° C., as can be measured in accordance with DIN ISO 2115. The higher the fraction of molecular weight regulator, the lower the minimum film formation temperature.

One of the ways in which the adjustment of the particle radii can be influenced is via the fraction of emulsifiers. The higher this fraction, more particularly at the beginning of the polymerization, the smaller the particles obtained.

As indicated above, the emulsion polymer may constitute a core-shell polymer, which may have one, two, three or more shells. In this case the segment obtainable by polymerizing the monomer mixture of the invention preferably forms the outermost shell of the core-shell polymer. The shell may be connected to the core or to the inner shells via covalent bonds.

Moreover, the shell may also be polymerized onto the core or onto an inner shell. In this embodiment the segment obtainable by ways including polymerizing the monomer mixture of the invention may in many cases be separated and isolated from the core by means of suitable solvents.

The core may be formed preferably of polymers comprising 50% to 100%, preferably 60% to 90%, by weight of units derived from (meth)acrylates. Preference here is given to esters of (meth)acrylic acid whose alcohol residue comprises preferably 1 to 30 carbon atoms, more preferably 1 to 20 carbon atoms and very preferably 1 to 10 carbon atoms. They include, more particularly, (meth)acrylates deriving from saturated alcohols, such as methyl (meth)acrylate, ethyl (meth)acrylate, n-propyl (meth)acrylate, isopropyl (meth)acrylate, n-butyl (meth)acrylate, tert-butyl (meth)acrylate, pentyl (meth)acrylate and hexyl (meth)acrylate.

The core can be prepared using a mixture which comprises methacrylates and acrylates. Thus it is possible more particularly to use mixtures of methyl methacrylate and acrylates having 2 to 10, preferably 2 to 8 carbon atoms, such as ethyl acrylate, butyl acrylate, hexyl acrylate and ethylhexyl acrylate. Of particular interest are monomer mixtures for preparing the core or one of the inner shells, if the core-shell polymer contains more than one shell, that contain at least 30%, more preferably at least 50% and very preferably at least 60% by weight of acrylates having 2 to 10 carbon atoms, based on the total weight of the monomer mixture for preparing the core or at least one of the inner shells.

Furthermore, the polymers of the core may comprise the comonomers set out above. In accordance with one preferred modification the core may be crosslinked. This crosslinking may be achieved through the use of monomers having two, three or more free-radically polymerizable double bonds.

The particle radius of the emulsion polymers can be within a wide range. Thus, in particular, it is possible to use emulsion polymers having a particle radius in the range from 10 to 500 nm, preferably 10 to 100 nm, more preferably 20 to 60 nm. More particularly, particle radii of below 50 nm may be advantageous for film formation and for the coating properties. The radius of the particles can be determined by means of PCS (Photon Correlation Spectroscopy), the data given relating to the r50 value (50% of the particles are smaller, 50% are larger). This can be done using, for example, a Beckman Coulter N5 Submicron Particle Size Analyzer.

The binder composition may further comprise one or more adjuvants selected from the group consisting of flow improvers, pigments, dyes, thickeners, rheology modifiers, defoamers, surfactants, stabilizers, preservatives, fungicides, algicides, flash rust inhibitors, coalescence agents, dispersing agents, corrosion inhibitors, and/or adhesion promoters.

The binder composition according to the present invention is particularly useful as a coating or adhesive material, preferably in paints, varnishes, impregnating compositions, adhesives and/or primers. These coating materials preferably have a minimum film formation temperature of not more than 50° C., more preferably not more than 35° C. and very preferably not more than 25° C., which can be measured in accordance with DIN ISO 2115, and can advantageously be used to coat woods, metals and plastics. For instance, coating materials for industrial coatings, and architectural paints, exhibit excellent performance capacities, it being possible for these coating materials to be used, for example, for the coating of furniture or floor coverings.

EXAMPLES

General Synthetic Procedure for Monomers

All reactions and product manipulations were carried out in common laboratory glassware under normal conditions. Methyl (meth)acrylate, (meth)acrylic anhydride (MAAH), (meth)acryloyl chloride, catalysts and solvents were obtained from commercial/industrial suppliers and used as received without further purification.

NMR spectra were recorded on Barker Avance 300 or 400 spectrometers at 300 K unless otherwise noted and internally referenced to residual solvent resonances ($^1$H NMR: THF-d8: 1.72 ppm, $C_6D_6$: 7.16 ppm, toluene-d8 (tol-d8): 2.08 ppm; $CDCl_3$: 7.26 ppm. $^{13}C\{^1H\}$ NMR: THF-d8: 25.31 ppm, $C_6D_6$: 128.06 ppm, $CDCl_3$: 77.16 ppm). Chemical shifts δ are given in ppm referring to external standards of tetramethylsilane ($^1$H, $^{13}C\{^1H\}$). $^1$H and $^{13}$C NMR signals were assigned partially based on 2D NMR spectra ($^1$H, $^1$H—COSY; $^1$H, $^{13}$C-HSQC; $^1$H, $^{13}$C-HMQC).

General Procedure I:

The urea-containing alcohol or amine (1.00 eq.), methylmethacrylate (10.0 eq.) and a polymerization inhibitor (e.g. MEHQ, 200 ppm) are weighed in a round bottom flask with mechanical stirring, air supply, sump temperature display, a filling element column set on it, as well as an automatically controlled column head with reflux and distillate cooler. Additional inhibitors may also be added. The mixture is heated to boiling and first a methyl methacrylate-water azeotrope is distilled off, until no more azeotrope distillate and instead pure methyl methacrylate distillate is observed (in case anhydrous starting materials are used, the removal of water via azeotrope-distillation is not necessary). The batch is cooled by about 10-20° C., and a catalyst (e.g. titanium isopropoxide (IPT) (1% rel. to alcohol) as well as methyl methacrylate, the amount being equivalent to the mass of the lost azeotrope distillate, are added.

Again, the mixture is heated to boiling, and the resulting methyl methacrylate-methanol azeotrope is distilled off at a reflux ratio of 2:1, up to a maximum head temperature of 70° C., and later at a reflux ratio of 10:1, until a constant column head temperature of 98-101° C. is reached. The reaction is typically terminated within 2 h-16 h. The batch is cooled to 80° C. When titanium alkoxides have been used as catalyst, diluted sulfuric acid followed by sodium carbonate is added. Optionally Tonsil or Celatom or Celite are added. The batch is filtered by pressure filtration (EKS pressure filter). The clear filtrate is optionally obtained as a solution in methyl methacrylate or concentrated under vacuum (RT to 125° C., ambient pressure or up to 1 mbar) until the product is obtained as a colourless oil or solid. Optionally, the product may be obtained as crystalline material upon cooling of the solution. Optionally, the product may be recrystallized from suitable common organic solvents, such as e.g. ethyl acetate, methanol, ethanol and acetone. Optionally, the product may be washed with suitable organic solvents, such as e.g. pentane, hexane, heptane, diethyl ether or toluene.

General Procedure II:

Methacrylic acid anhydride (1-5 eq.) and the catalyst (0.1-5 mol %) are mixed together, optionally with addition of a polymerization inhibitor (such as MEHQ, e.g. 200 ppm), and optionally with addition of an organic solvent (such as dichloromethane). The urea-containing alcohol or amine (1.00 eq.) is added and the resulting mixture is heated to 60° C.-90° C., upon which a homogeneous solution is obtained. During the reaction, air is constantly bubbled through the reaction mixture. After four hours, the mixture is cooled down, and the product precipitates from the solution. The product is filtered off, optionally washed with an organic solvent (e.g. heptane) and dried.

When an organic solvent was used, the reaction mixture at the end of the reaction is reacted with excess methanol in order to quench residual methacrylic anhydride. The resulting mixture is washed with hydrochloric acid (1 M, 2×) and sodium bicarbonate (saturated solution, 3×) and brine. The organic phase is dried and concentrated under vacuum, yielding the product as a colourless oil or solid.

The as-obtained product already contains co-precipitated inhibitor 2,4-Dimethyl-6-tert-butylphenol (arising from methacrylic anhydride) in sufficient amounts and does not have to be stabilized with polymerization inhibitors additionally. When MEHQ is added, the as-obtained product also contains co-precipitated inhibitor 4-methoxyphenol.

2-(3-phenylureido)ethyl Methacrylate (Prepared According to General Procedure II)

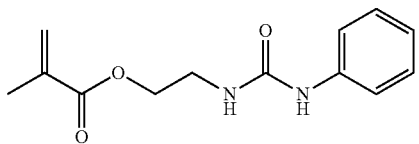 [SMILES: C=C(C)C(=O)OCCNC(=O)Nc1ccccc1]

Following general procedure II, methacrylic acid anhydride (115.6 g, 0.749 mol, 2.70 eq.) and the catalyst DMAP (0.339 g, 1 mol %) are mixed together, with addition of a polymerization inhibitor MEHQ (0.0138 g, 200 ppm). The urea-containing alcohol 1-(2-hydroxyethyl)-3-phenylurea 50 g, 0.277 mol, 1.00 eq.) is added and the resulting mixture is heated to 75° C., upon which a homogeneous solution is obtained. During the reaction, air is constantly bubbled through the reaction mixture. After four hours, the mixture is cooled down, and the product precipitates from the solution. It can also directly be obtained upon addition of n-heptane to the reaction mixture, which leads to precipitation of the product. The product is filtered off and dried. Yield: 55.9 g (81%).

$^1$H NMR (DMSO-d6, 400.13 MHz): δ [ppm]=1.89 (dd, $^4$J=1.5 Hz, $^4$J=1.0 Hz, 3H, $CH_3$), 3.39 (dt, $^3$J=5.5 Hz, $^3$J=5.8 Hz, 2H, $CH_2$), 4.14 (t, $^3$J=5.5 Hz, 2H, $CH_2$), 5.68

(dq, $^4J$=1.5 Hz, $^4J$=1.1 Hz, 1H, CH$_2$), 6.08 (bs, 1H, CH$_2$), 6.26 (t, $^3J$=5.8 Hz, 1H, NH), 6.89 (tt, $^3J$=7.4 Hz, $^4J$=1.1 Hz, 1H, CH), 7.18-7.24 (m, 2H, CH), 7.35-7.42 (m, 2H, CH), 8.52 (s, 1H, NH).
$^{13}$C{$^1$H} NMR (DMSO-d6, 100.61 MHz): δ [ppm]=17.9 (CH$_3$), 38.14 (CH$_2$), 63.9 (CH$_2$), 117.7 (CH), 121.1 (CH), 125.8 (CH$_2$), 128.6 (CH), 135.8 (C$_q$), 140.3 (C$_q$), 155.2 (CO), 166.5 (CO)

2-methyl-2-(3-phenylureido)propyl Methacrylate (Prepared According to General Procedure II)

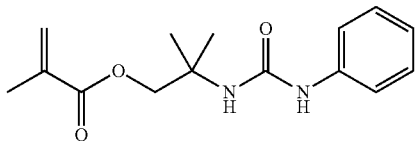 [SMILES: C=C(C)C(=O)OCC(C)(C)NC(=O)Nc1ccccc1]

$^1$H NMR (DMSO-d6, 400.13 MHz): δ [ppm]=1.30 (s, 6H, 2×CH$_3$), 1.90 (s, 3H, CH$_3$), 4.20 (s, 2H, CH$_2$), 5.68 (dq, $^4J$=1.5 Hz, $^2J$=1.1 Hz, 1H, CH), 6.08 (bs, 2H, NH and CH overlapping), 6.88 (tt, $^3J$=7.4 Hz, $^4J$=1.1 Hz, 1H, CH), 7.16-7.24 (m, 2H, CH), 7.30-7.35 (m, 2H, CH), 8.31 (s, 1H, NH).
$^{13}$C{$^1$H} NMR (DMSO-d6, 100.61 MHz): δ [ppm]=17.9 (CH$_3$), 24.4 (CH$_3$), 51.5 (C(CH$_3$)$_2$), 68.8 (OCH$_2$), 117.5 (CH), 120.9 (CCH$_2$), 125.7 (CH), 128.6 (CH), 135.8 (CCH$_2$), 140.3 (C$_q$), 154.4 (CO), 166.3 (CO).

3-(3-phenylureido)propyl Methacrylate (Prepared According to General Procedure I)

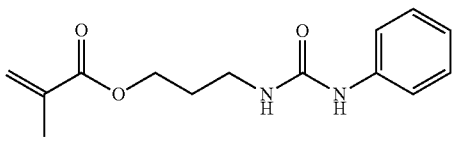 [SMILES: C=C(C)C(=O)OCCCNC(=O)Nc1ccccc1]

$^1$H NMR (DMSO-d6, 400.13 MHz): δ [ppm]=1.78 (q, $^3J$=6.7 Hz, 2H, CH$_2$), 1.89 (bs, 3H, CH$_3$), 3.18 (apparent q, $^3J$=6.6 Hz, 2H, CH$_2$), 4.14 (apparent t, $^3J$=6.4 Hz, 2H, CH$_2$), 5.65 (dq, $^4J$=1.5 Hz, $^4J$=1.1 Hz, 1H, CH$_2$), 6.05 (bs, 1H, CH$_2$), 6.18 (t, $^3J$=5.7 Hz, 1H, NH), 6.88 (tt, $^3J$=7.4 Hz, $^4J$=1.1 Hz, 1H, OH), 7.15-7.24 (m, 2H, OH), 7.34-7.42 (m, 2H, OH), 8.40 (s, 1H, NH).
$^{13}$C{$^1$H} NMR (DMSO-d6, 100.61 MHz): δ [ppm]=17.9 (CH$_3$), 28.9 (CH$_2$), 35.9 (CH$_2$), 62.1 (CH$_2$), 117.7 (CH), 121.0 (CH), 125.6 (CH$_2$), 128.6 (CH), 135.9 (C$_q$), 140.5 (C$_q$), 155.2 (CO), 166.6 (CO)

2-(2-(3-phenylureido)ethoxy)ethyl Methacrylate (Prepared According to General Procedure I)

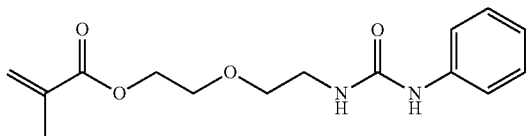 [SMILES: C=C(C)C(=O)OCCOCCNC(=O)Nc1ccccc1]

According to general procedure I, 290.1 g (2.898 mol, 10.0 eq.) methyl methacrylate, 65.33 g (0.291 mol, 1.00 eq.) 1-(2-(2-hydroxyethoxy)ethyl)-3-phenylurea, and 0.017 g hydroquinone monomethyl ether (200 ppm) as inhibitor are weighed in a 0.5 litre round bottom flask with mechanical stirring, air supply, sump temperature display, a filling element column set on it, as well as an automatically controlled column head with reflux and distillate cooler. Additional inhibitors may also be added.

The mixture is heated to boiling and first a methyl methacrylate-water azeotrope is distilled off, until no more azeotrope distillate and instead pure methyl methacrylate distillate is observed. The batch is cooled by about 10-20° C., and IPT (0.66 g, 1% rel. to alcohol) as well as methyl methacrylate, the amount being equivalent to the mass of the lost azeotrope distillate, are added.

Again, the mixture is heated to boiling, and the resulting methyl methacrylate-methanol azeotrope is distilled off at a reflux ratio of 2:1, up to a maximum head temperature of 70° C., and later at a reflux ratio of 10:1, until a constant column head temperature of 98-101° C. is reached. The reaction is typically terminated within 2 h-16 h. The batch is cooled to 80° C. and diluted sulfuric acid followed by sodium carbonate is added. Optionally Tonsil or Celatom or Celite are added. The batch is filtered and clarified by pressure filtration (EKS pressure filter). The clear filtrate is optionally obtained as a solution in methyl methacrylate or concentrated under vacuum (RT to 125° C., ambient pressure or up to 1 mbar) until the product 2-(2-(3-phenylureido)ethoxy)ethyl methacrylate is obtained as a colourless solid. Yield: 73.7 g (87%).

$^1$H NMR (DMSO-d6, 400.13 MHz): δ [ppm]=1.88 (dd, $^4J$=1.5 Hz, $^4J$=1.0 Hz, 3H, CH$_2$), 3.25 (dt, $^3J$=5.7 Hz, $^3J$=5.5 Hz, 2H, CH$_2$), 3.50 (t, $^3J$=5.5 Hz, 2H, CH$_2$), 3.65-3.69 (m, 2H, CH$_2$), 4.21-4.26 (m, 2H, CH$_2$), 5.65 (dq, $^4J$=1.5 Hz, $^4J$=1.5 Hz, 1H, CH$_2$), 6.02-6.06 (m, 1H, CH$_2$), 6.17 (t, 3J=5.7 Hz, 1H, NH), 6.83 (tt, $^3J$=7.4 Hz, '$J$=1.1 Hz, 1H, CH), 7.17-7.24 (m, 2H, CH), 7.34-7.40 (m, 2H, CH), 8.49 (s, 1H, NH).
$^{13}$C{$^1$H} NMR (DMSO-d6, 100.61 MHz): δ [ppm]=17.9 (CH$_3$), 38.9 (CH$_2$), 63.7 (CH$_2$), 68.0 (CH$_2$), 69.8 (CH$_2$), 117.6 (CH), 120.9 (CH), 125.8 (CH$_2$), 128.6 (CH), 135.8 (CO, 140.5 (C$_q$), 155.2 (CO), 166.5 (CO)

6-(3-phenylureido)hexyl Methacrylate (Prepared According to General Procedure I)

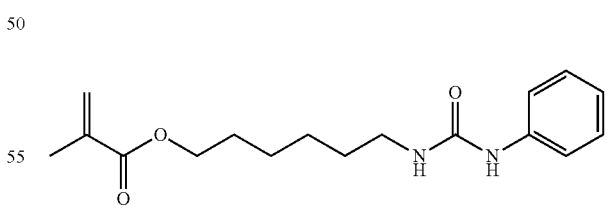

$^1$H NMR (DMSO-d6, 400.13 MHz): δ [ppm]=1.24-1.36 (m, 6H, CH$_2$), 1.56-1.68 (m, 2H, CH$_2$), 1.87 (bs, 3H, CH$_3$), 3.07 (dt, $^3J$=6.7 Hz, $^3J$=5.7 Hz, 2H, CH$_2$), 4.08 (t, $^3J$=6.4 Hz, 2H, CH$_2$), 5.62-5.65 (m, 1H, CH$_2$), 6.01 (bs, 1H, CH$_2$), 6.10 (t, $^3J$=5.5 Hz, 1H, NH), 6.86 (tt, $^3J$=7.2 Hz, $^4J$=1.1 Hz, 1H, CH), 7.16-7.24 (m, 2H, CH), 7.35-7.42 (m, 2H, CH), 8.37 (s, 1H, NH).
$^{13}$C{$^1$H} NMR (DMSO-d6, 100.61 MHz): δ [ppm]=17.9 (CH$_3$), 25.2 (CH$_2$), 26.0 (CH$_2$), 28.1 (CH$_2$), 29.6 (CH$_2$), 38.9 (CH$_2$), 64.2 (CH$_2$), 117.6 (CH), 120.8 (CH), 125.4 (CH), 128.6 (CH), 136.0 (C$_q$), 140.6 (C$_q$), 155.2 (CO), 166.6 (CO).

6-(3-cyclohexylureido)hexyl Methacrylate (Prepared According to General Procedure I)

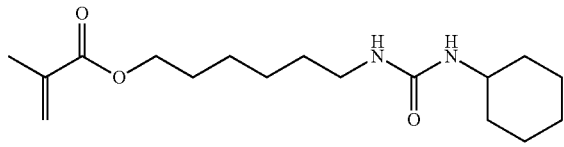 [SMILES: C=C(C)C(=O)OCCCCCCNC(=O)NC1CCCCC1]

$^1$H NMR (DMSO-d6, 400.13 MHz): δ [ppm]=0.96-1.17 (m, 3H, CH$_2$), 1.18-1.40 (m, 8H, CH$_2$), 1.45-1.55 (m, 1H, CH), 1.56-1.67 (m, 4H, CH$_2$), 1.67-1.77 (m, 2H, CH), 1.87 (s, 3H, CH$_3$), 2.95 (dt, $^3$J=6.7 Hz, $^3$J=6.3 Hz, 2H, CH$_2$), 3.26-3.40 (m, 1H, CH), 4.07 (t, $^3$J=6.8 Hz, 2H, CH$_2$), 5.56-5.70 (m, 3H, CCH$_2$ and NH), 6.00 (s, 1H, NH).

$^{13}$C{$^1$H} NMR (DMSO-d6, 100.61 MHz): δ [ppm]=17.9 (CH$_3$), 24.4 (CH$_2$), 25.2 (CH$_2$), 25.3 (CH$_2$), 26.0 (CH$_2$), 28.0 (CH$_2$), 29.9 (CH$_2$), 33.3 (CH$_2$), 39.0 (CH$_2$NH), 47.6 (CH), 64.1 (CH$_2$O), 125.3 (CH$_2$), 135.9 (CCH$_2$), 157.3 (CO), 166.5 (CO).

The invention claimed is:

1. A compound of the general formula (I):

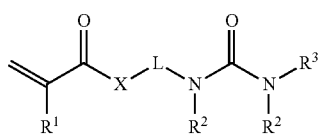

(I)

wherein
R$^1$ is Me;
R$^2$ is —H;
R$^3$ is selected from phenyl and cyclohexyl;
X is —O—; and
L is selected from the group consisting of: butyl, hexyl, and ethoxyethyl.

2. A composition, comprising:
the compound according to claim 1, and
at least one polymerization inhibitor.

3. A process for preparing the compound according to claim 1, the process comprising:
reacting a urea containing alcohol or amine of the general formula (II)

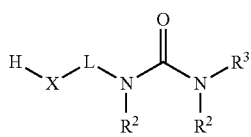

(II)

wherein
X is —O—;
R$^2$ is —H;
R$^3$ is selected from phenyl and cyclohexyl; and
L is selected from the group consisting of: butyl, hexyl, and ethoxyethyl, with a (meth)acrylate species, (meth)acryloyl chloride, (meth)acrylic acid or (meth)acrylic anhydride;
wherein said (meth)acrylate species is an alkyl (meth)acrylate of the general formula (III)

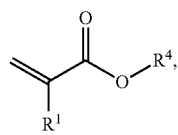

(III)

wherein R$^4$ is methyl, ethyl, propyl or butyl.

4. A binder composition, comprising:
at least one polymer including at least one repeating unit derived from the compound according to claim 1.

5. The binder composition according to claim 4, wherein the at least one polymer is made of a monomer mixture comprising between 0.25 wt. % and 20 wt. % of the compound.

6. The binder composition according to claim 4, wherein the polymer further comprises at least one repeating unit of or derived from (meth)acrylic acid, (meth)acrylate, styrene, a styrene derivative, and/or a vinyl ester.

7. The binder composition according to claim 4, wherein the at least one polymer is an emulsion polymer.

8. The binder composition according to claim 7, wherein the emulsion polymer is a core-shell polymer.

9. The binder composition according to claim 7, wherein a particle radius of the emulsion polymer is in the range from 10 to 500 nm.

10. The binder composition according to claim 4, further comprising:
one or more adjuvants selected from the group consisting of a flow improver, a pigment, a dye, a thickener, a rheology modifier, a defoamer, a surfactant, a stabilizer, a preservative, a fungicide, an algaecide, a flash rust inhibitor, a coalescence agent, a dispersing agent, a corrosion inhibitor, and an adhesion promoter.

11. A method of coating or adhering, comprising:
applying a composition comprising the binder composition according to claim 4, to a surface.

12. The method according to claim 11, wherein the composition is a paint, a varnish, an impregnating composition, an adhesive, or a primer.

* * * * *